(12) United States Patent
Kawai et al.

(10) Patent No.: US 7,038,036 B2
(45) Date of Patent: May 2, 2006

(54) OLIGONUCLEOTIDES LABELED WITH STABLE ISOTOPES AND A METHOD FOR DETECTING THE SAME

(75) Inventors: Gota Kawai, Chiba-Ken (JP); Akira Wada, Chiba-Ken (JP); Hiroshi Takaku, Chiba-Ken (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 380 days.

(21) Appl. No.: 10/214,503

(22) Filed: Aug. 7, 2002

(65) Prior Publication Data

US 2003/0104433 A1 Jun. 5, 2003

Related U.S. Application Data

(62) Division of application No. 09/535,786, filed on Mar. 28, 2000, now abandoned.

(30) Foreign Application Priority Data

Mar. 31, 1999 (JP) ................................. 11-094323

(51) Int. Cl.
*C07H 21/04* (2006.01)
(52) U.S. Cl. ..................... 536/24.5; 436/173
(58) Field of Classification Search ............... 536/23.1, 536/24.5; 530/324; 436/173
See application file for complete search history.

(56) References Cited

OTHER PUBLICATIONS

"Comparative Pharmacokinetics, Tissue Distribution, and Tumor Accumulation of Phosphorothioate, Phosphorodithioate, and Methylphosphonate Oligonucleotides in Nude Mice" R.K. DeLong, A Nolting, M. Fisher, Q. Chen, E. Wickstrom, M. Kligshteyn, S. Demirdji, M. Caruthers, and R.L. Juliano / Antisense & Nucleic Acid Drug Development &:71-77 (1997) Mary Ann Liebert, Inc. / P. 71-77.

"Research Techniques Applicable to Pediatrics—Stable Isotope Breath Tests" Lawrence T Weaver / Department of Child Health, University of Glasgow, Yorkhill Hospital, Glasgow, Scotland, UK / Nutrition vol. 14, No. 10, 1998 / p. 826-829.

"Measurement of cell proliferation by labeling of DNA with stable isotope-labeled glucose: Studi s in vitro, in animals, and in humans" D. Macallan, C. Fullerton, R. Neese, K. Haddock, S. Park, and M. Hellersten / Medical Science vol. 95 Jan. 1998 / p. 708-713.

"Helicobacter pylori" B. Dunn, H. Cohen and M. Blaser / Clinical Microbiology Reviews, vol. 10, No. 4, Oct. 1997 / p. 720-741.

Title: "Targeting of Cancer-Related Proteins with PNA Oligomers" Margus Pooga and Ulo Langel From the Current Cancer Drug Targets, vol. 1, No. 3, 2001, Pp. 231-239.

Title: "Antisense Anticancer Oligonucleotide Therapeutics" Hui Wang, Gautam Prasad, John K. Buolamwini and Ruiwen Zhang From the Current Cancer Drug Targets, vol. 1, No. 3, 2001, Pp. 177-196.

Title: "Oligonucleotides Comprised of Alternating 2'-Deoxy-2'-fluoro-β-D-arabinonucleosides and D-2'-deoxyribonucleosides (2'F-ANA/DNA 'Altimer') Induce Effcient RNA Cleavage Mediated by Rnase H" Kyung-Lyum Min, Ekaterina Viazovkina, Annie Galarneau, Michael A. Parniak and Masad j. Damha From the Bioorganic & Medicinal Chemistry Letters, vol. 12, Issue 18, Sep. 16, 2002, Pp 2651-2654.

(Continued)

*Primary Examiner*—Andrew Wang
*Assistant Examiner*—Tracy Vivlemore
(74) *Attorney, Agent, or Firm*—J.C. Patents

(57) ABSTRACT

Antisense oligonucleotide sequences which enable the measurement of the distribution and structure of antisense oligonucleotide drugs in the body, with lapse of time, and a method of detecting these sequences are provided. The antisense chains have a natural or non-natural nucleotide or peptide nucleic acid as a structural unit in which carbon atoms and nitrogen atoms are substituted by $^{13}C$ and $^{15}N$, respectively, and the antisense chains can be detected by nuclear magnetic resonance spectroscopy (NMR) such as $^{15}N$—$^{1}H$ or $^{13}C$—$^{1}H$ hetero nuclear multiple quantum coherence spectroscopy.

2 Claims, 15 Drawing Sheets

OTHER PUBLICATIONS

Title: "Magnetic Resonance Pharmacoangiography to Detect and Predict Chemotherapy Delivery to Solid Tumors" Dmitri Artemov, Meiyappan Solaiyappan and Zaver m. Bhujwalla From Cancer Research vol. 61, Apr. 1, 2001, by American Association for Cancer Research, Pp 3039-3044 Article also can be found at http://cancerres.aacrjournals.org/cgi/content/full/61/7/3039.

Title: "Antiproliferative effect in chronic myeloid leukaemia cells by antisense peptide nucleic acids" Valentina Rapozzi, Brigitte E. A. Burm, Susanna Cogoi, Gijs A. van Boom, Franco Quadrifoglio and Luigi E. Xodo From the Nucleic Acids Research, Sep. 1, 2002, vol. 30, No. 17, by Oxford University Press, Pp. 3712-3721 Article also can be found at http://pubmedcentral.nih.gov/articlerender.fcgi?tool=pubmed&pubmedid=12202756.

Title: "Cellular uptake of antisense oligonucleotides after complexing or conjugation with cell-penetrating model peptides" J. Oehlke, P. Birth, E. Klauschenz, B. Wiesner, M. Beyermann, A. Oksche and M. Bienert From the FEBS Journal (European Journal of Biochemistry) vol. 269, Issue 16, Aug. 2002, Pp. 4025-4032 Article also can be found at http://content.febsjournal.org/cgi/content/full/269/16/4025.

SEQUENCE LISTING

```
<160> NUMBER OF SEQ ID NOS: 1

<210> SEQ ID NO 1
<211> LENGTH: 43
<212> TYPE: RNA
<213> ORGANISM: Artificial
<220> FEATURE:
<223> OTHER INFORMATION: Designed oligonucleotide based on size
      and stability

<400> SEQUENCE: 1
gggagagggc aaccugaccu guuaucaucg caagaagcuu ccg                    43
```

OLIGONUCLEOTIDES LABELED WITH STABLE ISOTOPES AND A METHOD FOR DETECTING THE SAME

CROSS-REFERENCE TO RELATED APPLICATION

This application is a divisional application of, and claims the priority benefit of, U.S. application Ser. No. 09/535,786 filed on Mar. 28, 2000, now abandoned, which claims the priority benefit of Japanese application Ser. No 11-094323, filed on Mar. 31, 1999.

BACKGROUND OF THE INVENTION

1. Technical Field of the Invention

The present invention relates to methods for detecting antisense oligonucleotides and peptide nucleic acids which are labeled with stable isotopes, and foreign antisense chains.

2. Background of the Invention

In recent years, antisense drugs using antisense technology have drawn attention as therapeutic agents for diseases such as cancers, genetic diseases and AIDS. An antisense drug refers to an oligonucleotide or the like that has a sequence complementary (antisense) to a part of a sequence of a specific gene which causes a certain disease. When introduced into the body (target cells), the antisense drug forms a specific double strand chain with mRNA, which is a transcription product of the causative gene, or a precursor thereof, to inhibit translation or processing of the precursor mRNA. Thus, this inhibition can control the onset of the disease. The efficacy of antisense drugs heavily depends on the technique to deliver the oligonucleotides to the target site. This is because nucleases that decompose nucleic acids are generally present in the body and digest the introduced oligonucleotides before they reach the target site, which disables the formation of the complementary double strand chains at the target site, thus no effect can be obtained. For example, a nucleic acid incorporated into a cell by endocytosis is incorporated into a lysosome in the cell, and then decomposed by a nuclease in the lysosome. Thus, the introduced oligonucleotide cannot form a double strand chain with the target transcription product in the nucleus or cytoplasm, resulting in no effect. An example of a useful delivery technique to solve this problem is the use of intracellular routing agents, typically represented by a liposome preparation, which has provided a certain level of success.

Another attempt to improve the effect of antisense drugs involves increasing the stability of the antisense chains by modifying the nucleotides, the structural units of oligonucleotides, to non-natural modified nucleotides which are less susceptible to decomposition by nucleases.

In developing therapeutic drugs, pharmacokinetic tests for absorption, metabolism and excretion of the drugs are carried out. In pharmacokinetic tests, substances to be tested (drugs) are labeled with radioactive isotopes or the like and administered to experimental animals, and the concentration and radioactivity of the drugs are quantitatively measured with the lapse of time. Antisense drugs are no exception and antisense oligonucleotides labeled with radioactive isotopes or the like are subjected to pharmacokinetic tests.

In the use of antisense oligonucleotide drugs, the sequence and length of the nucleotides have to be conserved in body cells to fully implement their function. However, conventional pharmacokinetic tests using radioisotopes or the like provide information on the distribution in the body, absorption rate, and excretion rate of the oligonucleotides but not on the conservation of their sequence and length. Accordingly, the state of the conservation of oligonucleotides has to be confirmed by extracting a nucleic acid fraction from blood, organs or the like taken from experimental animals to analyze oligonucleotides in the fraction by high performance liquid chromatography, Southern blotting, Northern blotting, capillary electrophoresis, or the like. Furthermore, it was virtually impossible to see the change in the length of the administered antisense nucleotides with the lapse of time (the progress of decomposition). Further, there is no means to confirm whether the target mRNA or precursor mRNA and the oligonucleotide introduced into cells form complementary double strand chains. Moreover, the efficacy of the introduction of the oligonucleotide can only be judged cytologically based on physiological or morphological changes of the cells to which the oligonucleotide is introduced. Furthermore, in conventional pharmacokinetic tests, the use of radioisotopes is inevitable, which requires a special facility according to specified regulations and well-trained technicians.

SUMMARY OF THE INVENTION

The present invention was made in consideration of the abovementioned problem and an objective of the present invention is to provide antisense oligonucleotide sequences and antisense peptide nucleic acid sequences labeled with stable isotopes, which enables the measurement of the distribution, state of conservation and structure of antisense oligonucleotide drugs in the body, with the lapse of time, and a method of detecting these sequences.

DETAILED DESCRIPTION OF THE PREFERRED EMBODIMENTS

Figure 1:
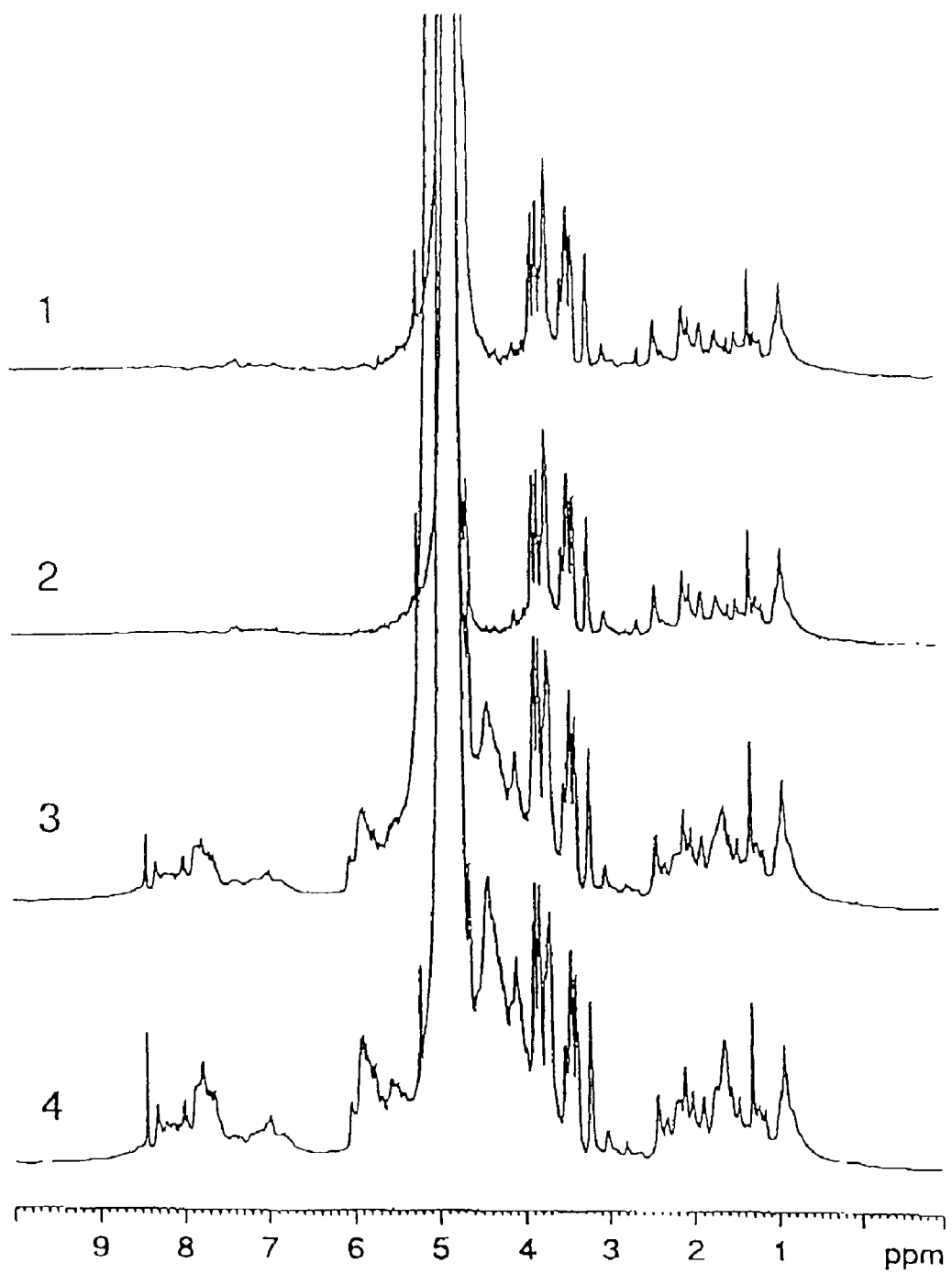
FIG. 1 shows 500 MHz $^1$H-NMR spectra of non-exchangeable protons for samples 1 to 4.

In order to solve the abovementioned problem and attain the abovementioned objective, the present invention is constituted as follows. Namely, an antisense oligonucleotide sequence and antisense peptide nucleic acid sequence of the present invention are single strand RNAs or single strand or double strand DNAs comprising at least one nucleotide or peptide nucleic acid as a structural unit, in which at least one structural C atom is substituted with $^{13}C$, and at least one structural N atom is substituted by $^{15}N$, having 10 to 100 bases complementary to the desired target sequence to be hybridized. In these antisense oligonucleotide sequence and antisense peptide nucleic acid sequence, said oligonucleotide is 1) a natural oligonucleotide wherein 3'-OH and 5'-OH in ribose or deoxyribose are cross-linked by phosphodiester bonds,
2) a phosphorothioate oligonucleotide wherein one or two non-cross-linked oxygen atoms in the phosphodiester bonds in said natural oligonucleotide are substituted by sulfur atoms, or
3) a methylphosphonate oligonucleotide wherein oxygen atoms in the hydroxyl groups in the phosphodiester bonds in said natural oligonucleotide are substituted by methyl groups, and said peptide nucleic acid has bases, i.e., purine or pyrimidine, and said bases are linked together by peptide bonds to form a 2-aminoethylglycine backbone.

In an antisense oligonucleotide sequence and an antisense peptide nucleic acid sequence of the present invention, it is preferable that all carbon atoms are substituted by $^{13}C$, and all nitrogen atoms are substituted by $^{15}N$ in all structural units, i.e., nucleotides and peptide nucleic acids.

A composition of the present invention comprises the abovementioned antisense oligonucleotide sequence or antisense peptide nucleic acid sequence, and a pharmaceutically acceptable carrier.

A method of detecting an antisense oligonucleotide sequence containing stable isotopes or decomposition products thereof, or an antisense peptide nucleic acid sequence containing stable isotopes or decomposition products thereof, comprises a step of sampling at least one material to be measured, i.e., blood, tissues, organs, body fluids, cells or excretions from a subject animal to which an antisense oligonucleotide sequence or antisense peptide nucleic acid sequence having a sequence complementary to a desired target sequence to form a hybrid is administered, or a step of sampling subject culture cells to which an antisense oligonucleotide sequence or antisense peptide nucleic acid sequence having a sequence complementary to a desired target sequence to form a hybrid is administered, and a step of measuring the antisense oligonucleotide or antisense peptide nucleic acid derived from said sampled material to be measured, by nuclear magnetic resonance spectrometry, said antisense oligonucleotide sequence or antisense peptide nucleic acid sequence being the abovementioned antisense oligonucleotide sequence or antisense peptide nucleic acid sequence of the present invention.

A method of detecting an oligonucleotide sequence containing stable isotopes and decomposition products thereof, or an antisense peptide nucleic acid sequence containing stable isotopes and decomposition products thereof comprises a step of subjecting a subject animal administered with the abovementioned antisense oligonucleotide sequence or antisense peptide nucleic acid sequence of the present invention to magnetic resonance imaging.

An antisense oligonucleotide sequence and antisense peptide nucleic acid sequence of the present invention are explained as follows.

The nucleotide sequence and peptide nucleic acid (hereinafter occasionally referred to as an antisense chain in this invention), the structural unit of an antisense oligonucleotide sequence and antisense peptide nucleic acid sequence respectively of the present invention, is a natural nucleotide or non-natural nucleotide, or a peptide nucleic acid. Examples of a natural nucleotide include purine nucleotides, such as adenosine and guanosine nucleotide, and pyrimidine nucleotides, such as thymidine, uridine and cytidine nucleotide. Examples of a non-natural nucleotide include phosphorothioate nucleotides, in which one or two oxygen atoms of the phosphoryl group are substituted by sulfur atoms, and methylphosphonate nucleotides, in which an oxygen atom of a hydroxyl group in the phosphoryl group is substituted by a methyl group, and peptide nucleic acids, artificial nucleotides, in which a base is introduced into a 2-aminoethyl glycine framework.

Furthermore, in these structural units, at least one carbon atom, a structural atom, is substituted by $^{13}C$, and at least one nitrogen atom, a structural atom, is substituted by $^{15}N$. By substituting carbon atoms in an antisense chain, the presence of the antisense chain in a material to be measured can be confirmed by nuclear magnetic resonance spectrometry such as $^{13}C$—$^{1}H$ heteronuclide multiple quantum coherence spectrometry (hereinafter referred to as HMQC method) and $^{13}C$—$^{1}H$ heteronuclide single quantum coherence spectrometry (hereinafter referred to as HSQC method). Further, by substituting nitrogen atoms in an antisense chain, whether the antisense chain has formed base pairs can be confirmed by nuclear magnetic resonance spectrometry such as $^{15}N$—$^{1}H$ HMQC method and $^{5}N$—$^{1}H$ HSQC method).

A target of an antisense chain of the present invention is a known sequence and can be appropriately selected depending on the purpose. In consideration of the best balance between the cost for the synthesis of the antisense chain, and the capability for stable hybridization with the target sequence, the length of the antisense chain is preferably 10 to 100 bases, more preferably 15 to 50 bases. If the length of the antisense chain is less than 10 bases, stable hybridization with the target sequence in vitro is rather difficult. On the other hand, if the length of the antisense chain is more than 100 bases, the synthesis of the antisense chain containing stable isotopes costs a great deal, which is not preferable. An antisense chain of the present invention is synthesized using a sequence, in which carbon atoms and nitrogen atoms of the structural unit, i.e., a nucleotide or peptide nucleic acid, are substituted by concentrated $^{13}C$ and $^{15}N$, according to a method known to one skilled in the art. The structural unit used in the synthesis is available, for example, from Nippon Sanso Corporation, and a method for the synthesis is described in detail in Japanese Patent Laid-open No. 1994-319581 and Japanese Patent Laid-open No. 1995-115987. Accordingly, an antisense chain of the present invention synthesized by this method contains $^{13}C$ and $^{15}N$ in a higher ratio than the corresponding natural chain. It is preferable that more than 90% of the carbon atoms and nitrogen atoms in the molecule are substituted by $^{13}C$ and $^{15}N$.

In the antisense oligonucleotide sequence or antisense peptide nucleic acid sequence, it is preferable that structural atoms, i.e., carbon atoms and nitrogen atoms, in every structural unit (nucleotide or peptide nucleic acid) are substituted by $^{13}C$ or $^{15}N$. By substituting all carbon atoms by $^{13}C$, signals arising from a $^{13}C$-labeled antisense chain can be selectively detected without detecting many other substances in which structural carbon atoms are $^{12}C$. On the other hand, by substituting all nitrogen atoms by $^{15}N$, signals arising from $^{15}N$-labeled antisense chains can be selectively detected without detecting many other substances in which structural nitrogen atoms are $^{14}N$. Furthermore, when labeled by $^{15}N$, an imino group proton for each base pair can be detected and distinguished, which can provide information on hydrogen bonding between each base (secondary structure).

A method for detecting an antisense chain of the present invention will be explained as follows.

First, at least one material to be measured, i.e., blood, tissues, organs, body fluids, cells or excretions, is sampled from a subject animal to which an isotope-labeled antisense oligonucleotide sequence or antisense peptide nucleic acid sequence having a sequence complementary to the desired target sequence to form hybrid, or from subject culture cells to which the similar sequence has been administered. A method of administering the antisense chain to the subject animal or subject culture cells is not particularly restricted, and various intracellular routing agents, such as liposome, e.g., lipofectin, and various drug delivery systems, such as a system using a histone subunit can be used. The antisense chain to be administered is not restricted to the isotope-labeled antisense oligonucleotide sequence and antisense peptide nucleic acid sequence, and compositions comprising these sequences and a pharmaceutically acceptable carrier can be used. Examples of a pharmaceutically acceptable carrier include liposomes such as lipofectin and nucleotide binding proteins such as histone protein.

The time of sampling of the material to be measured from the subject animal or subject culture cells are determined depending on the purpose. Namely, the sampling can be carried out immediately after the administration of the antisense chain, or approximately several to 10 days after the administration, taking into consideration the time required to release the antisense chain from liposome or the like into the cells.

The material to be measured is then measured by nuclear magnetic resonance spectrometry. In some cases, an appropriate pretreatment is carried out. For example, if the material to be measured is a fluid, such as blood or a body fluid, it is preferable to carry out nuclear magnetic resonance spectrometry after removing solids by centrifugation. If the sampled material to be measured is a solid, such as tissues or cells, it is necessary to homogenize the tissues and cells in a buffer solution, in which pH, salt concentration, and the like are adjusted, to extract a nucleic acid component, before the measurement by nuclear magnetic resonance spectrometry. The buffer solution and conditions for the homogenization can be appropriately determined by one skilled in the art depending on the material to be measured.

In the measurement by nuclear magnetic resonance spectrometry, it is preferable that the concentration of the antisense chain to be measured is 0.1 mM to 10 mM, and the concentration is appropriately adjusted before the measurement. About 5 to 10% of heavy water must be added to the pretreated material to be measured for the lock signal.

Nuclear magnetic resonance spectrometry is preferably performed by the one-dimensional or two-dimensional measurement using either HMQC method or HSQC method for $^{15}N$—$^1H$ and $^{13}C$—$^1H$. In this case, it is more preferable to carry out coherence selection by the pulse field gradient (PFG) method, or to remove solvent signals.

Measurement of $^{13}C$—$^1H$ by HMQC method or HSQC method indicates whether the antisense chain is contained in the material being measured, and if contained, the concentration can be determined. Measurement of $^{15}N$—$^1H$ by HMQC method or HSQC method indicates whether base pairs are formed in the material being measured. Using these methods, a pre-measured spectrum of the whole-length antisense chain and a spectrum of the antisense chain in the material sampled from the subject animal are compared to analyze whether the antisense chain being measured has been shortened by decomposition, or has been maintained over its whole length. Furthermore, a pre-measured spectrum of a double strand chain of the whole-length antisense chain with a target sequence, which is formed in vitro, and a spectrum of the antisense chain in the material sampled from the subject animal are compared to determine whether the antisense chain being measured forms a double strand chain with the target sequence. Further, combination with a quantitative analysis can advantageously make the analysis more sensitive.

In the present invention, magnetic resonance imaging can be used instead of the abovementioned nuclear magnetic resonance spectrometry. An antisense chain can be administered to a subject animal in the same manner as for nuclear magnetic resonance spectrometry. After administration, the subject animal or subject culture cell conjugate is subjected to magnetic resonance imaging devise for the measurement without the isolation of the material to be measured from the subject animal, or any pretreatment. In particular, when an animal is used as the subject, the state of absorption, secretion and excretion of the antisense chain in the body can be quantitatively observed and monitored with the lapse of time.

An antisense chain and a method for detecting the antisense chain can be used in various ways besides the abovementioned pharmacokinetic test. Examples of other uses include the diagnosis and treatment of diseases, such as cancers, genetic diseases, AIDS and influenza, and the evaluation of novel intracellular routing agents and drug delivering systems.

When applied to the diagnosis of diseases, the detection method of the present invention can be carried out in the same manner as for pharmacokinetic tests. Nuclear magnetic resonance spectrometry can be used to measure whether the antisense chain forms a double strand chain with a target sequence in cells or blood in cases where the diagnosis will be made using sample cells or blood that can be extracted from the body. Nuclear magnetic imaging can be used to measure whether the antisense chain forms a double strand chain with a target sequence in tissues or organs in cases where the diagnosis will be made using tissues and organs that cannot be excised from the body, For the treatment of the abovementioned diseases, an antisense chain of the present invention can be appropriately used to confirm whether the treatment is effective or not, by nuclear magnetic resonance spectrometry or magnetic resonance imaging. Accordingly, the present invention can be used in treating diseases, and is useful in determining the amount and interval of administration of the antisense drug to patients.

In developing a novel intracellular routing agent or drug delivery system, an evaluation of its effectiveness is necessary. The effectiveness of the drug introduction can be evaluated by the detection method of the present invention using an antisense chain of the present invention.

EXAMPLES

An experiment was carried out to confirm whether a RNA labeled with stable isotopes was detectable by NMR when the RNA was administered to mice.

Materials

Four female SPF/VAF mice (BALB/cAnNCr, 8 weeks old, No. 1 to No. 4) supplied by Charles River Japan, Inc. were used for the experiment.

A nucleotide labeled with $^{13}$C and $^{15}$N was synthesized by the method described in Japanese Patent Laid-open No. 1994-319581 and Japanese Patent Laid-open No. 1995-115987. An outline of this synthesizing method will be described as follows.

First, yeast cells of Candida utilis IFO-0369 were cultured in an inorganic medium using $^{13}$C-labeled acetic acid ($^{13}$CH$_3$$^{13}$COOH) as a carbon source and $^{15}$N-labeled ammonium chloride ($^{15}$NH$_4$Cl) as a nitrogen source, and then harvested. Cell walls were decomposed by a cell wall lytic enzyme, zymolyase (Kirin Breweries, Ltd.), after which the supernatant obtained by centrifugation was further centrifuged (100,000 g×3 hours) to obtain a ribosome fraction as a precipitate. Then, this ribosome fraction was treated with an equivalent amount of an aqueous saturated phenol solution to remove proteins, and then ethanol was added to precipitate a $^{13}$C- and $^{15}$N-labeled RNA.

The precipitate was washed with ethanol and dried under vacuum to obtain $^{13}$C- and $^{15}$N-labeled RNA of greater than 90% purity. This RNA was decomposed into ribonucleotide 5'-phosphates using nuclease P1 (Yamasa Shoyu Co.), and then the ribonucleotide 5'-phosphates were fractionated with an anion exchange column, AG1X8 formic acid-type (Bio-Rad), to obtain AMP, CMP, UMP and GMP.

Next, two phosphate groups were enzymatically added to each of the abovementioned AMP, CMP, UMP and GMP using phosphoenol pyruvic acid as a phosphate donor to obtain ribonucleotide 5'-triphosphates labeled with $^{13}$C and $^{15}$N, according to the method of Whitesides et al. (J. Org. Chem. 55, 1834–1841, 1990).

The oligonucleotide comprising 43 bases shown in SEQ ID No. 1 was synthesized using the abovementioned ribonucleotide 5'-triphosphate labeled with $^{13}$C and $^{15}$N, as a substrate. Synthesis was carried out using a synthesized DNA (a product of Hokkaido System Science; purified by HPLC) as a template, and T7RNA polymerase (Air Brown). After synthesis, the reaction solution was subjected to polyacrylamide gel electrophoresis for purification, and the resulting target band was cut with the gel from which RNA was extracted. The extracted RNA was twice precipitated with ethanol to remove salts, and the RNA labeled with $^{13}$C and $^{15}$N was obtained.

A mixture of histone subunits H2A, H2B, H3 and H4 (Boehringer Mannheim GmbH) was used as a drug delivery system.

Experimental Method

The abovementioned oligonucleotide (5 mg) was dissolved in 120 μl of a physiological saline solution to prepare four 3 μl samples. Two samples were administered without a drug delivery system. The abovementioned histone subunit mixture was added to the remaining two samples to form a complex.

Sample 1: $^{13}$C—$^{15}$N-labeled RNA (inoculated into and sampled from No. 1 mouse)

Sample 2: $^{13}$C—$^{15}$N-labeled RNA (inoculated into and sampled from No. 2 mouse)

Sample 3: the complex of $^{13}$C—$^{15}$N-labeled RNA and the drug delivery system (inoculated into and sampled from No. 3 mouse)

Sample 4: the complex of $^{13}$C—$^{15}$N-labeled RNA and the drug delivery system (inoculated into and sampled from No. 4 mouse)

Each sample solution (100 μl), which was adjusted to 62.5 mg/kg, was inoculated into the tail of the abovementioned mice. Three hours after the inoculation, the mice were anesthetized with ether and about 1 ml of whole blood was sampled from the heart. This whole blood was allowed to stand at room temperature for 30 minutes, and then centrifuged at 1,500 rpm at room temperature for 15 minutes. Supernatant serum obtained by the centrifugation was subjected to NMR measurement as follows. Heavy water (20 μl) was added to the samples (400 μl each) obtained by the abovementioned centrifugation, and the measurement of NMR spectra was carried out at 25° C. A DRX-500 NMR spectrometer (BRUKER) was used for the measurement. Pre-saturation was carried out for the measurement of non-exchangeable protons and jump-and-return pulses were used for the measurement of exchangeable imino proton spectra.

Results of the Measurements

FIGS. 1 to 15 show results of the measurements. The stable isotope-labeled oligonucleotide of the present invention was barely detected in all cases when no complex with the drug delivery system was formed, while the entire length of the oligonucleotide was detected when a complex with the drug delivery system was formed. Details will be explained referring to the drawings.

Evaluation

FIG. 1 shows the spectra of non-exchangeable protons for samples 1 to 4 measured at 500 MHz-$^1$H. Marks 1 to 4 designate samples 1 to 4, respectively. Signals derived from nucleic acid bases were observed mainly in the range of 9 to 6.5 ppm. A close look of this range shows that only extremely weak signals were detected for samples 1 and 2 which were administered without the drug delivery system. On the other hand, distinctive signals were detected in this range for samples 3 and 4 which were administered with the drug delivery system. Therefore, it is obvious that the antisense chain existed in the blood for up to 3 hours when the drug delivery system was used.

Figure 2:
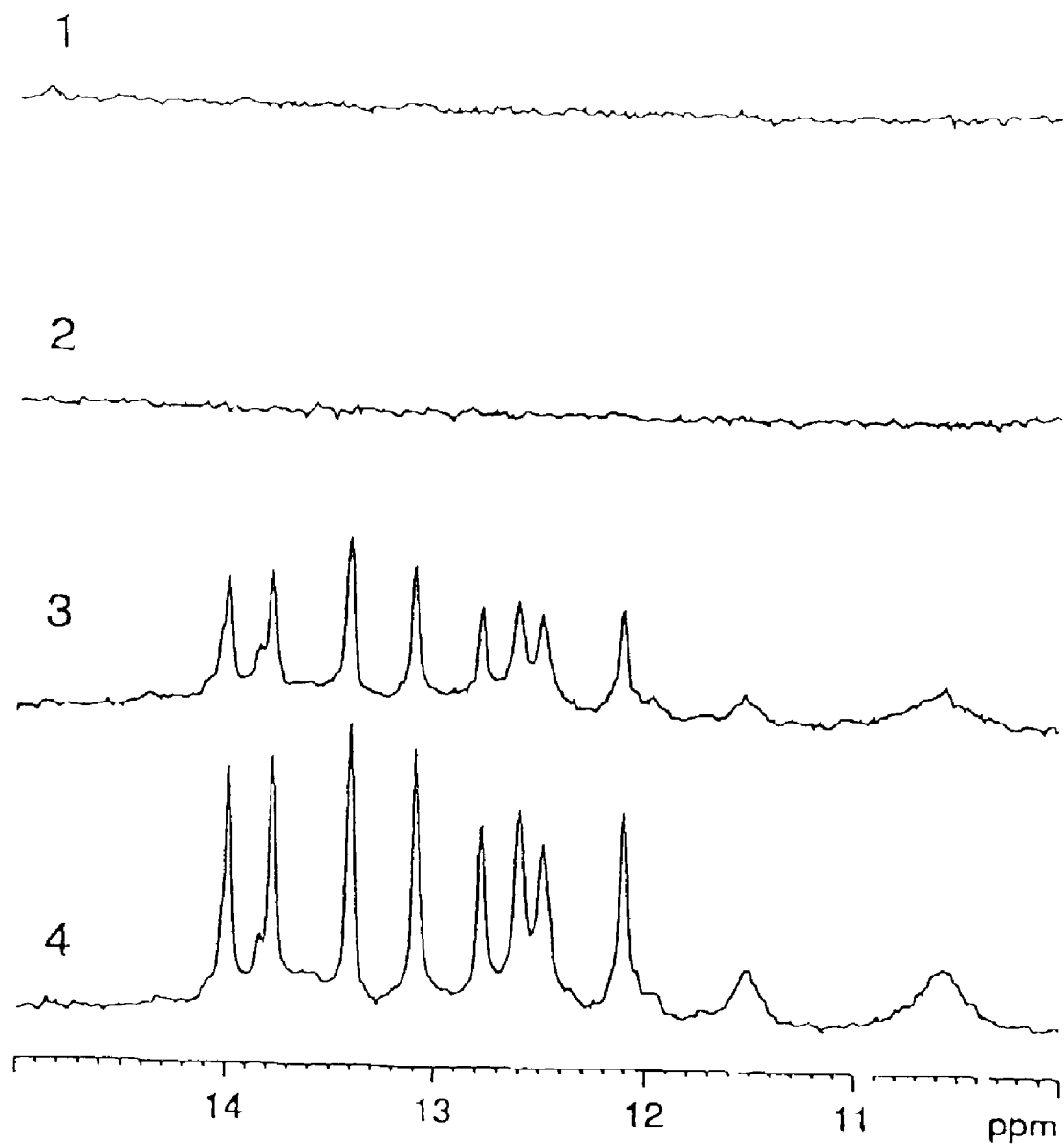
FIG. 2 shows 500 MHz $^1$H-NMR spectra of exchangeable protons for samples 1 to 4.

FIG. 2 shows the spectra of exchangeable protons (imino protons) for samples 1 to 4 measured at 500 MHz-$^1$H. Marks 1 to 4 designate samples 1 to 4, respectively. Signals derived from base pairs, which were stabilized by forming a secondary structure, were observed in the range shown in this figure. Absolutely no signal was detected for samples 1 and 2, but a set of strong, sharp signals were observed for samples 3 and 4. Therefore, these results suggest that the RNA present in the blood did not undergo partial decomposition when the drug delivery system was used. Such sharp signals would not have been observed and the spectra should have been more complex had the RNA undergone partial decomposition.

Figure 3:
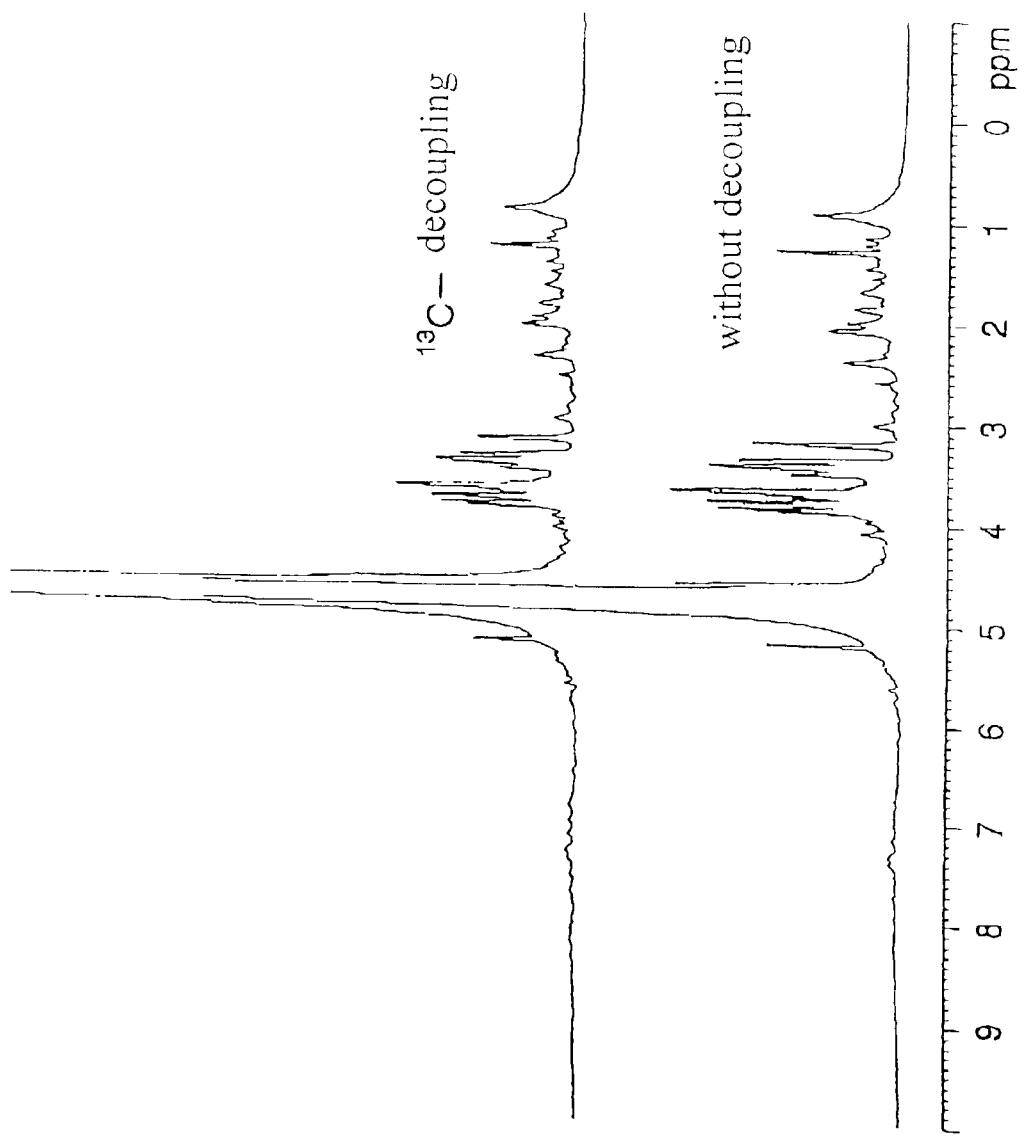
FIG. 3 shows 500 MHz $^1$H-NMR spectra of non-exchangeable protons for sample 1.
Figure 4:
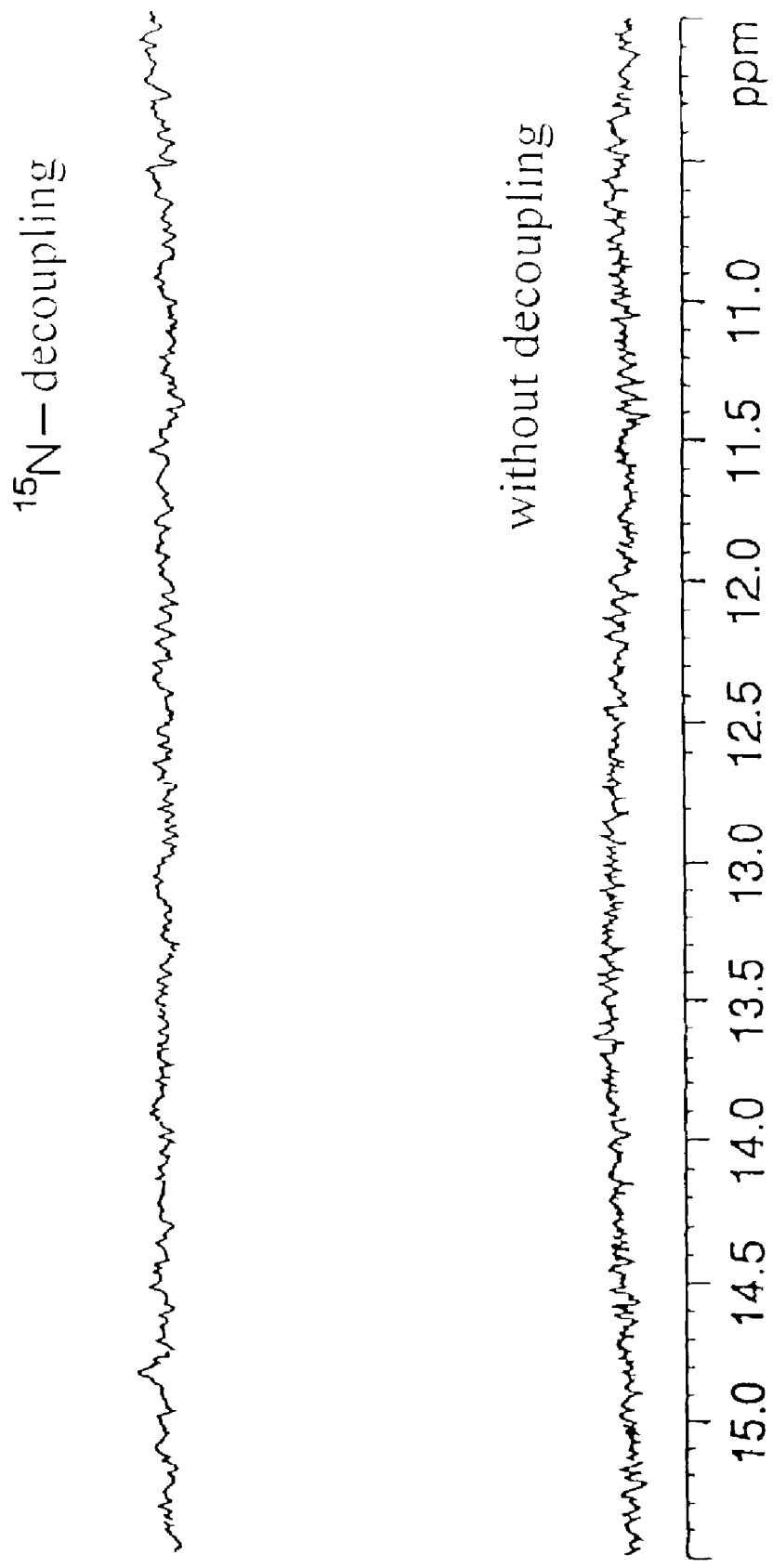
FIG. 4 shows 500 MHz $^1$H-NMR spectra of exchangeable protons for sample 1.

FIGS. 3, 6, 8 and 12 show the 500 MHz $^1$H-NMR spectra of non-exchangeable protons for samples 1 to 4. Comparison of these spectra shows that RNA was barely detected for samples 1 and 2, but clearly detected for samples 3 and 4. Comparison of the top and the bottom of FIGS. 3 and 4 shows that the spectrum in the range between 9 and 6.5 ppm was changed by decoupling, which indicates that the signals in this range were derived from the labeled RNA. Further, the signals observed at 8.4 ppm in FIG. 8 and FIG. 12 were not changed by decoupling, which suggests that the signals were derived from the drug delivery system.

Figure 9:
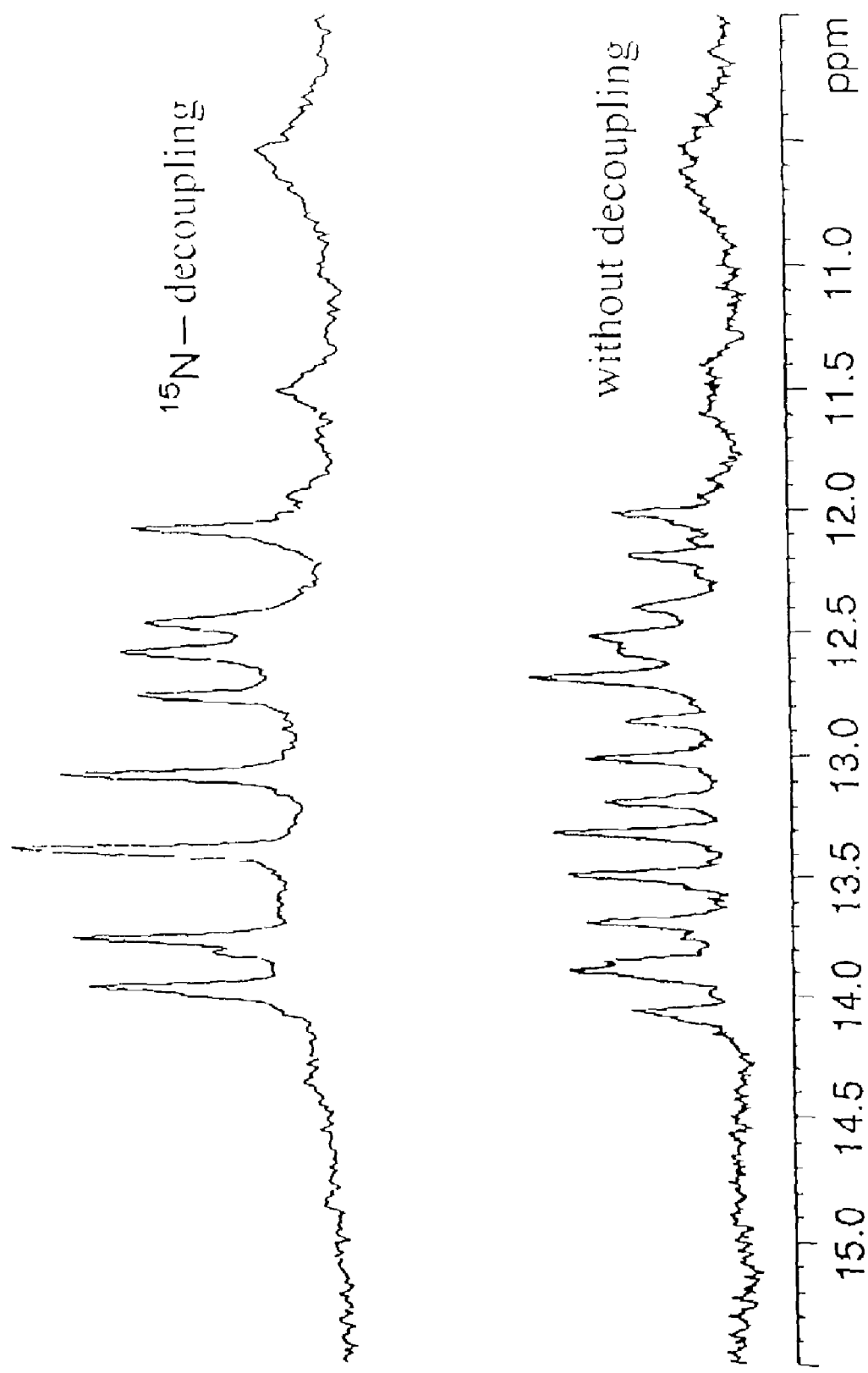
FIG. 9 shows 500 MHz $^1$H-NMR spectra of exchangeable protons for sample 3.
Figure 13:
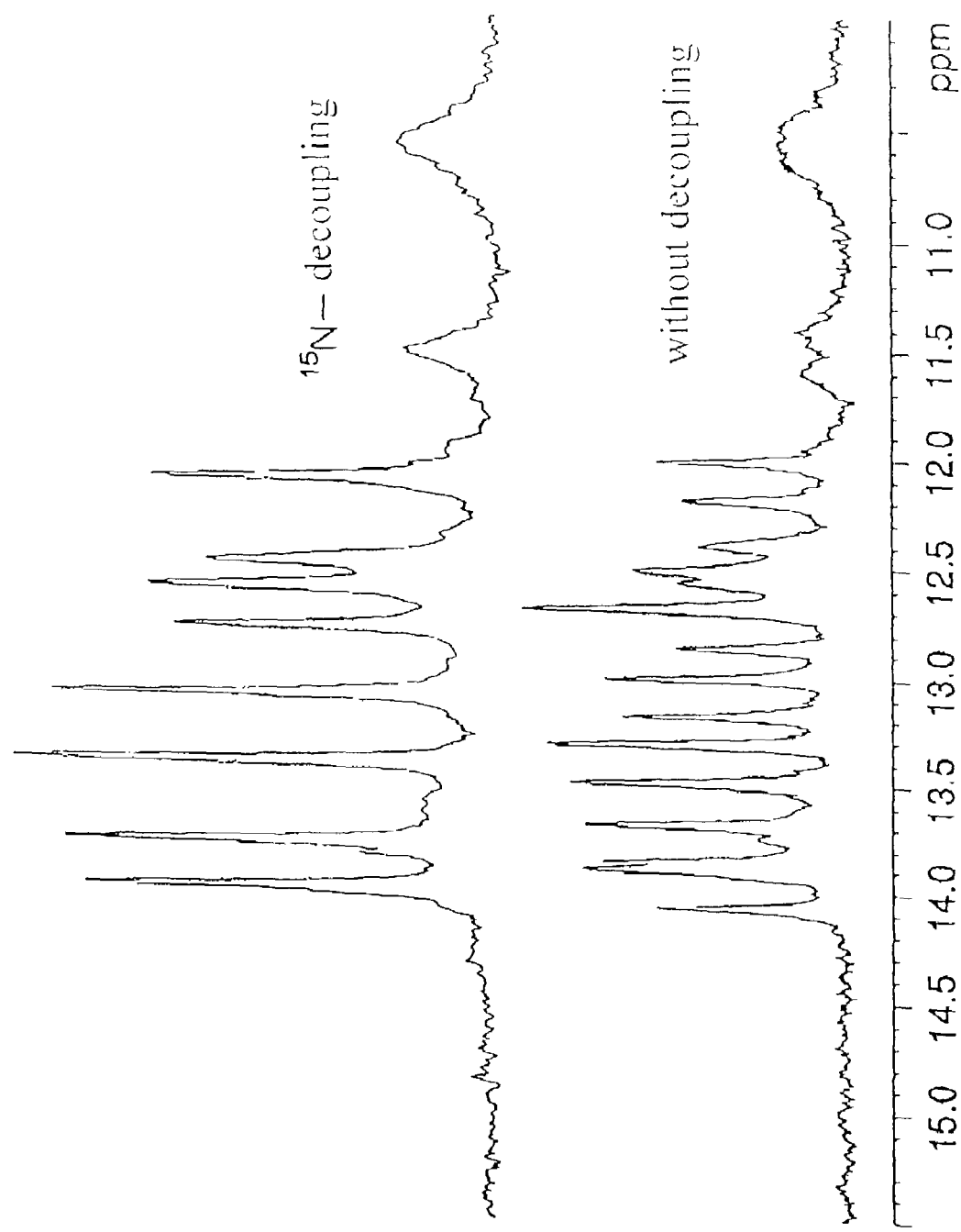
FIG. 13 shows 500 MHz $^1$H-NMR spectra of exchangeable protons for sample 4.

FIGS. 4, 7, 9 and 13 show the 500 MHz $^1$H-NMR spectra of exchangeable protons for samples 1 to 4. Comparison of these spectra shows that the RNA was barely detected for samples 1 and 2, but clearly detected for samples 3 and 4. Comparison of the top and the bottom of FIGS. 9 and 13 shows that the entire spectrum in this range was changed by decoupling, which shows that the signals in this range were derived from the labeled RNA.

Figure 5:
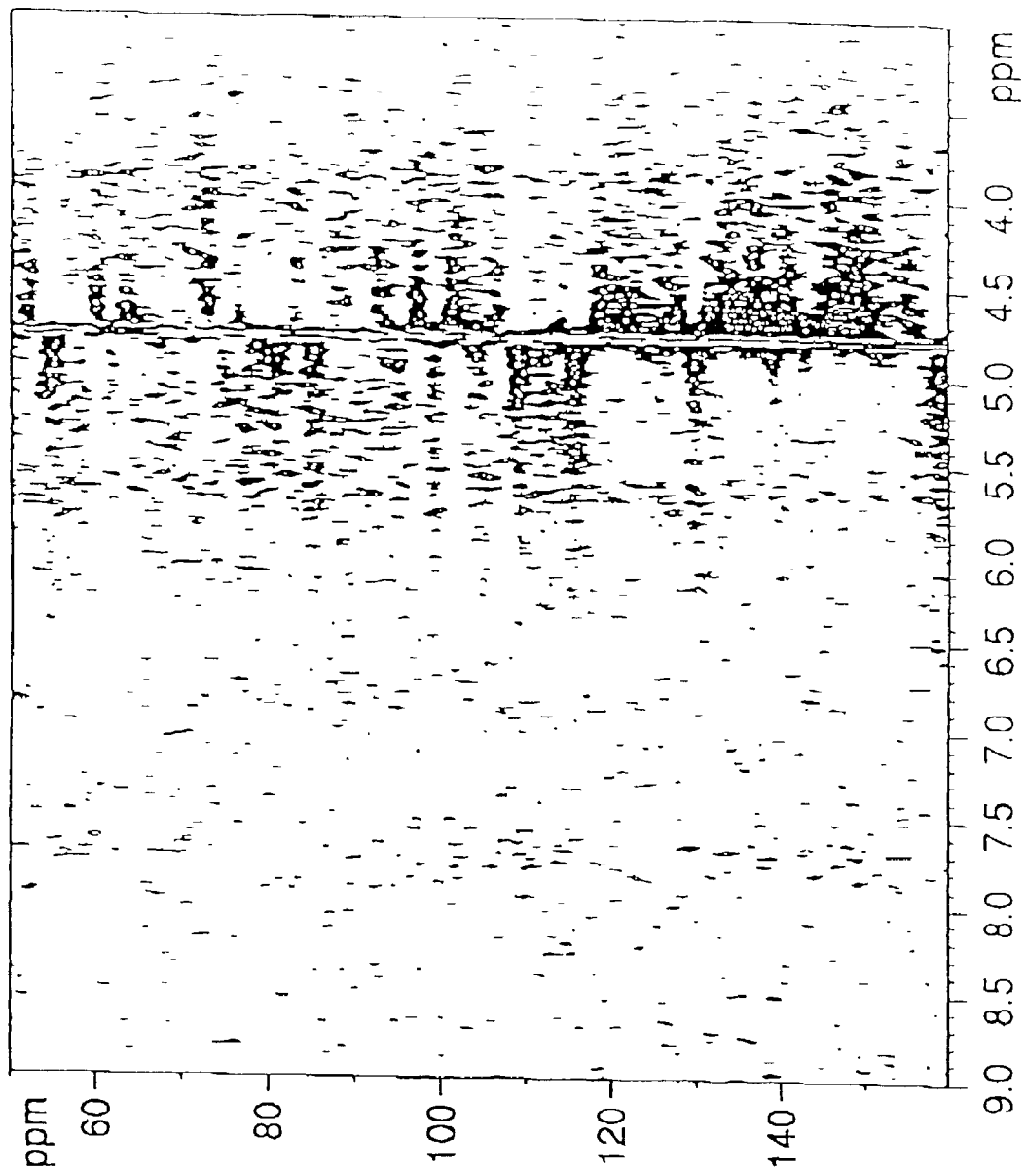
FIG. 5 shows 500 MHz $^{13}$C—$^1$H HMQC spectra of non-exchangeable protons for sample 1.
Figure 6:
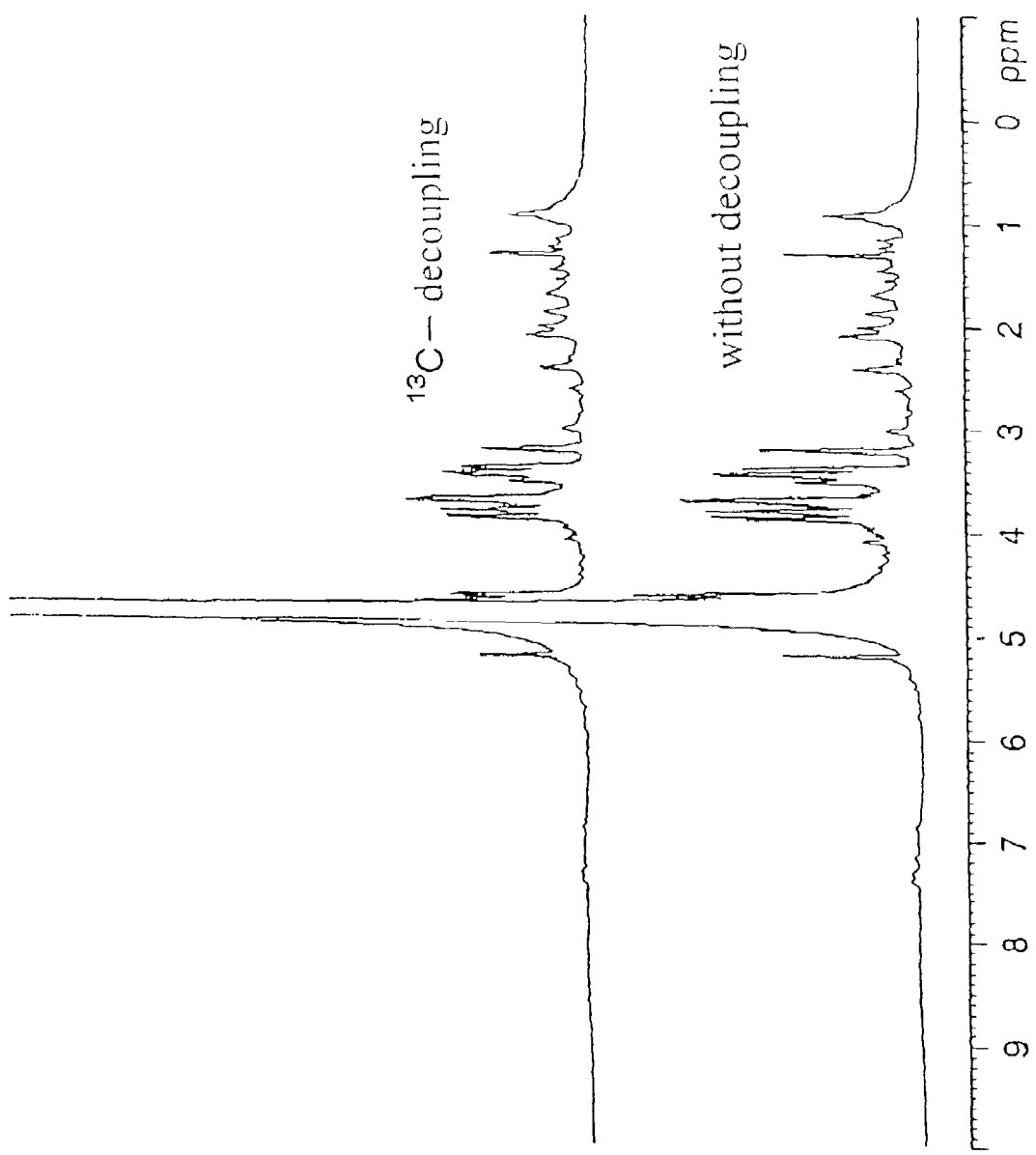
FIG. 6 shows 500 MHz $^1$H-NMR spectra of non-exchangeable protons for sample 2.
Figure 7:
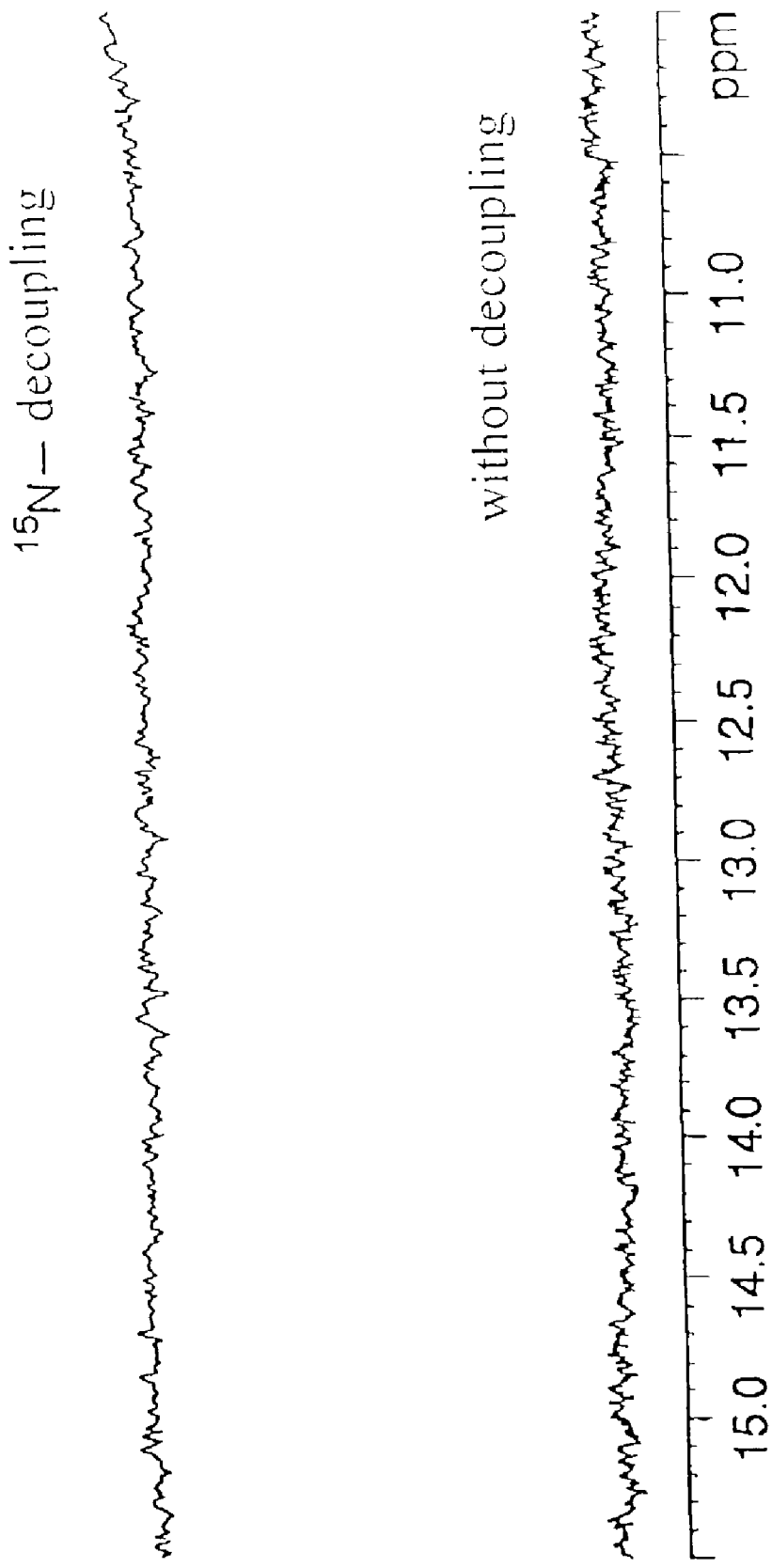
FIG. 7 shows 500 MHz $^1$H-NMR spectra of exchangeable protons for sample 2.
Figure 8:
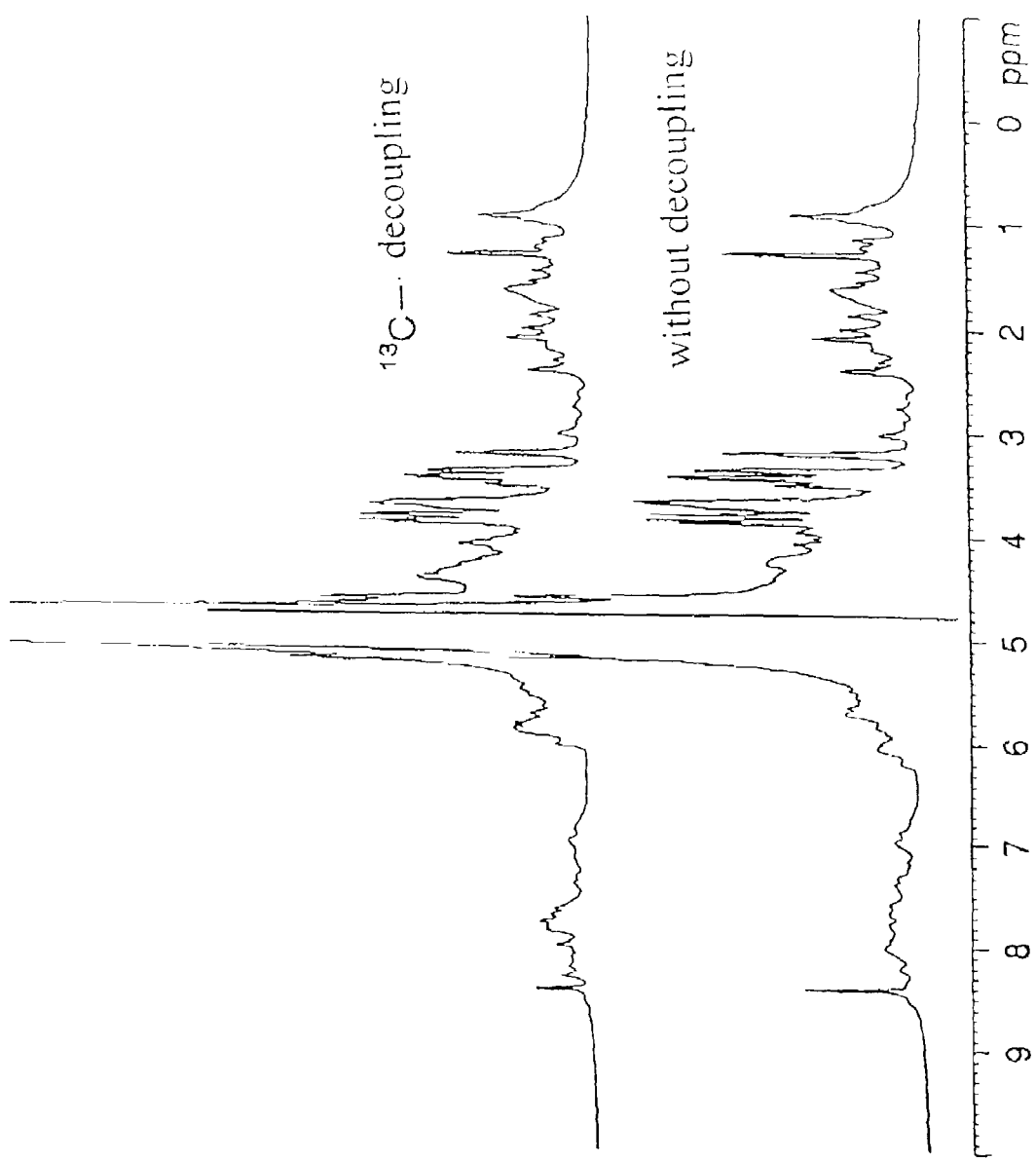
FIG. 8 shows 500 MHz $^1$H-NMR spectra of non-exchangeable protons for sample 3.
Figure 10:
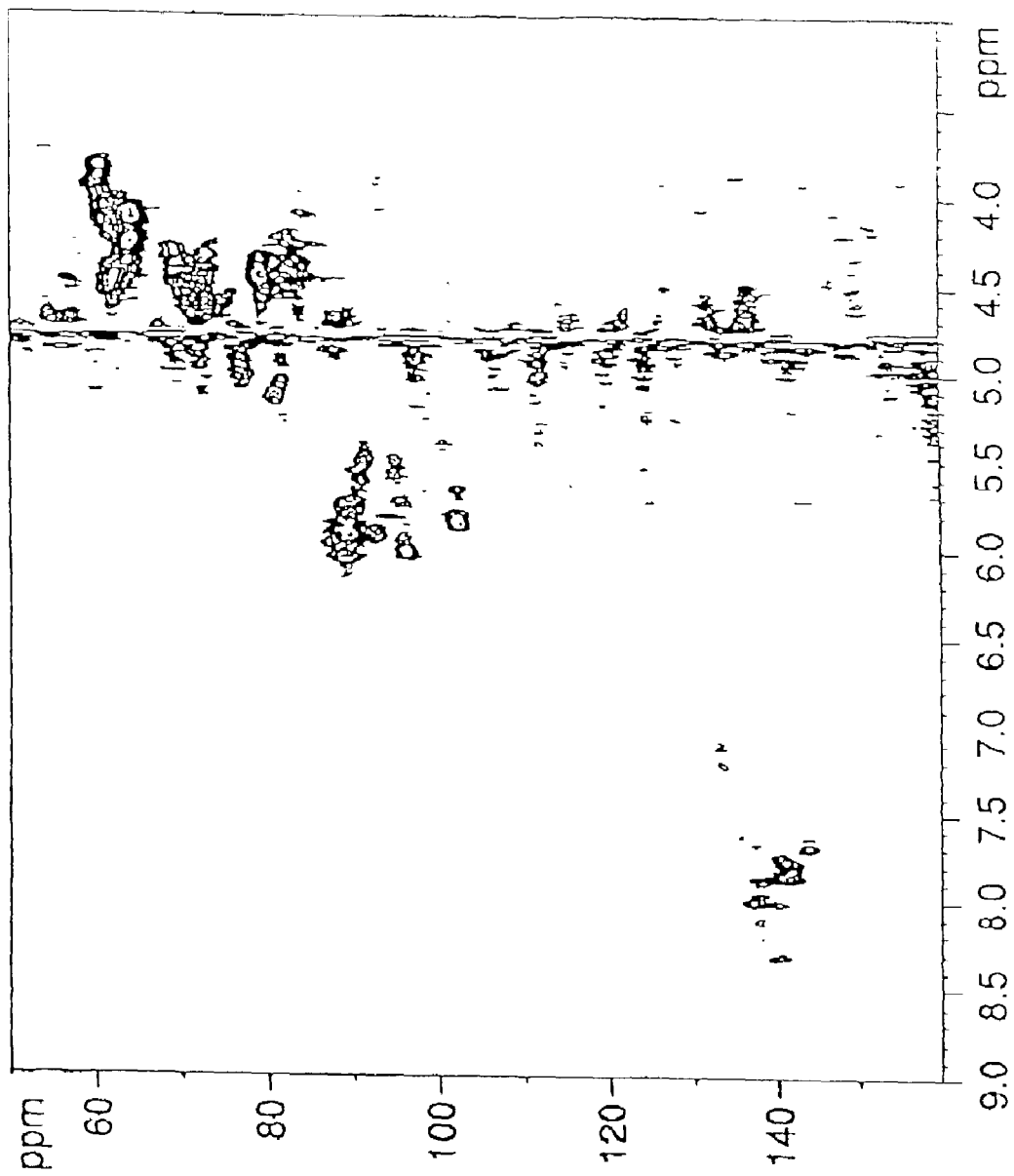
FIG. 10 shows 500 MHz $^{13}$C—$^1$H HMQC spectra of non-exchangeable protons for sample 3.
Figure 14:
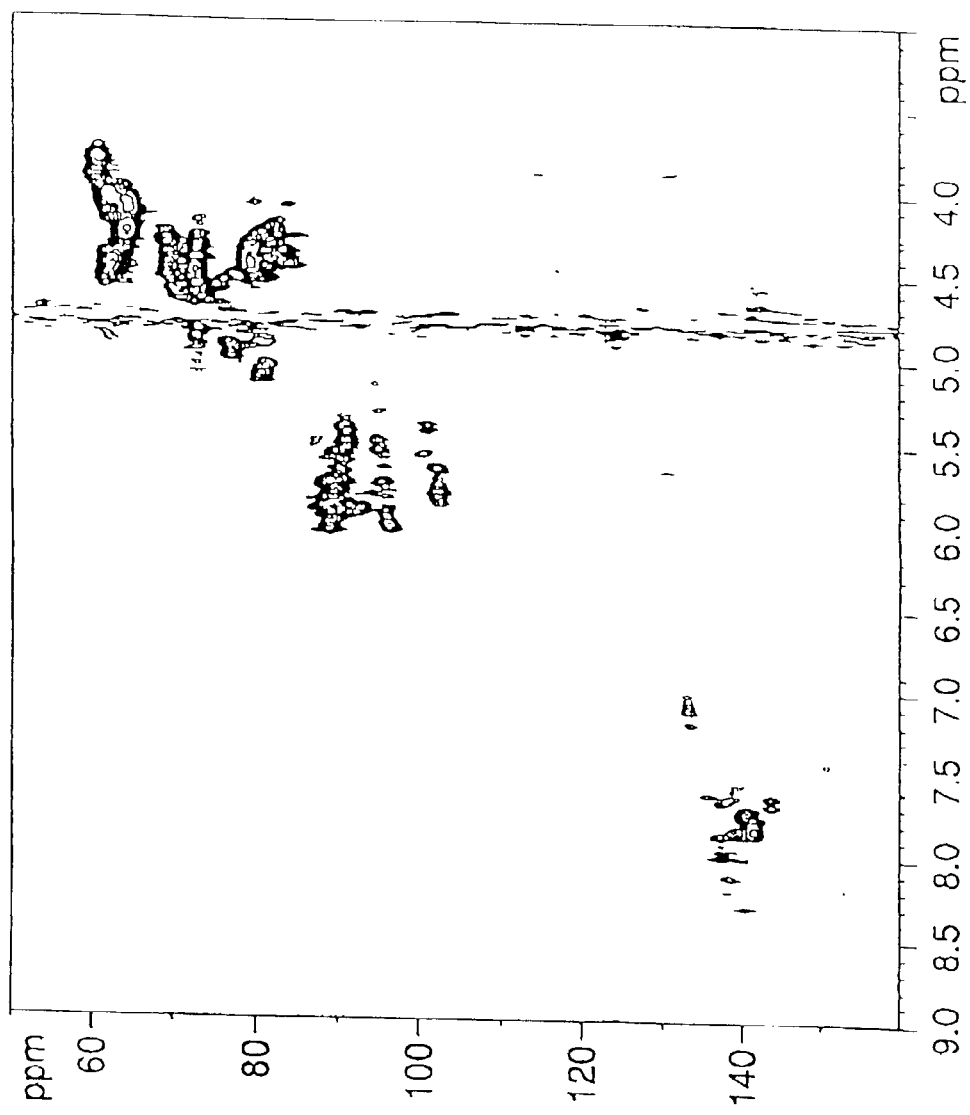
FIG. 14 shows 500 MHz $^{13}$C—$^1$H HMQ spectra of non-exchangeable protons for sample 4.

FIGS. 5, 10 and 14 show the $^{13}$C—$^1$H HMQC spectra of non-exchangeable protons for samples 1, 3 and 4. The vertical axis is the $^{13}$C chemical shift and the horizontal axis is the $^1$H chemical shift. Only noise, and no spectrum derived from RNA, was observed for sample 1. On the other hand, spectra for samples 3 and 4 showed typical RNA patterns.

Figure 11:
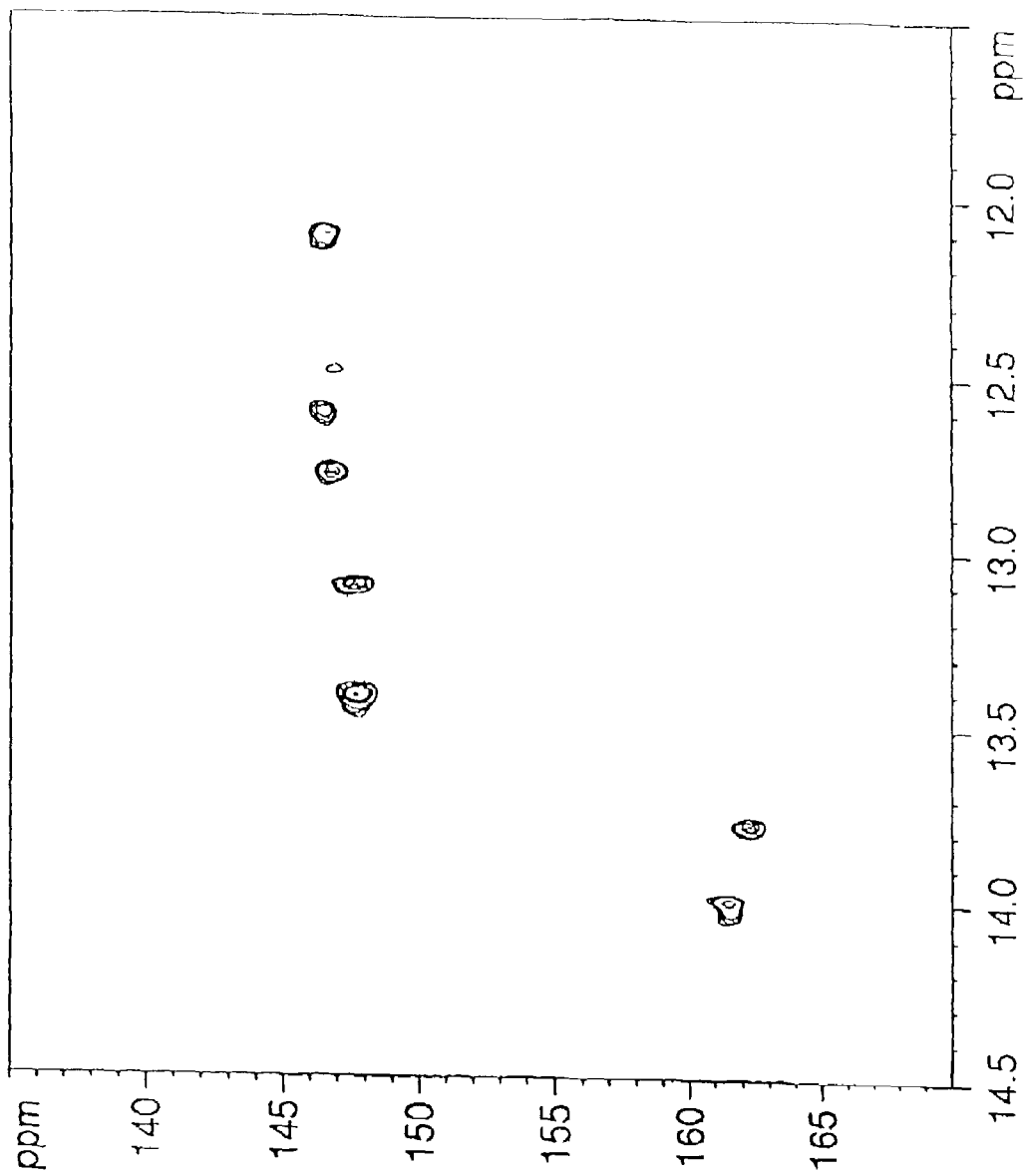
FIG. 11 shows 500 MHz $^{15}$N—$^1$H HMQC spectra of non-exchangeable protons for sample 3.
Figure 12:
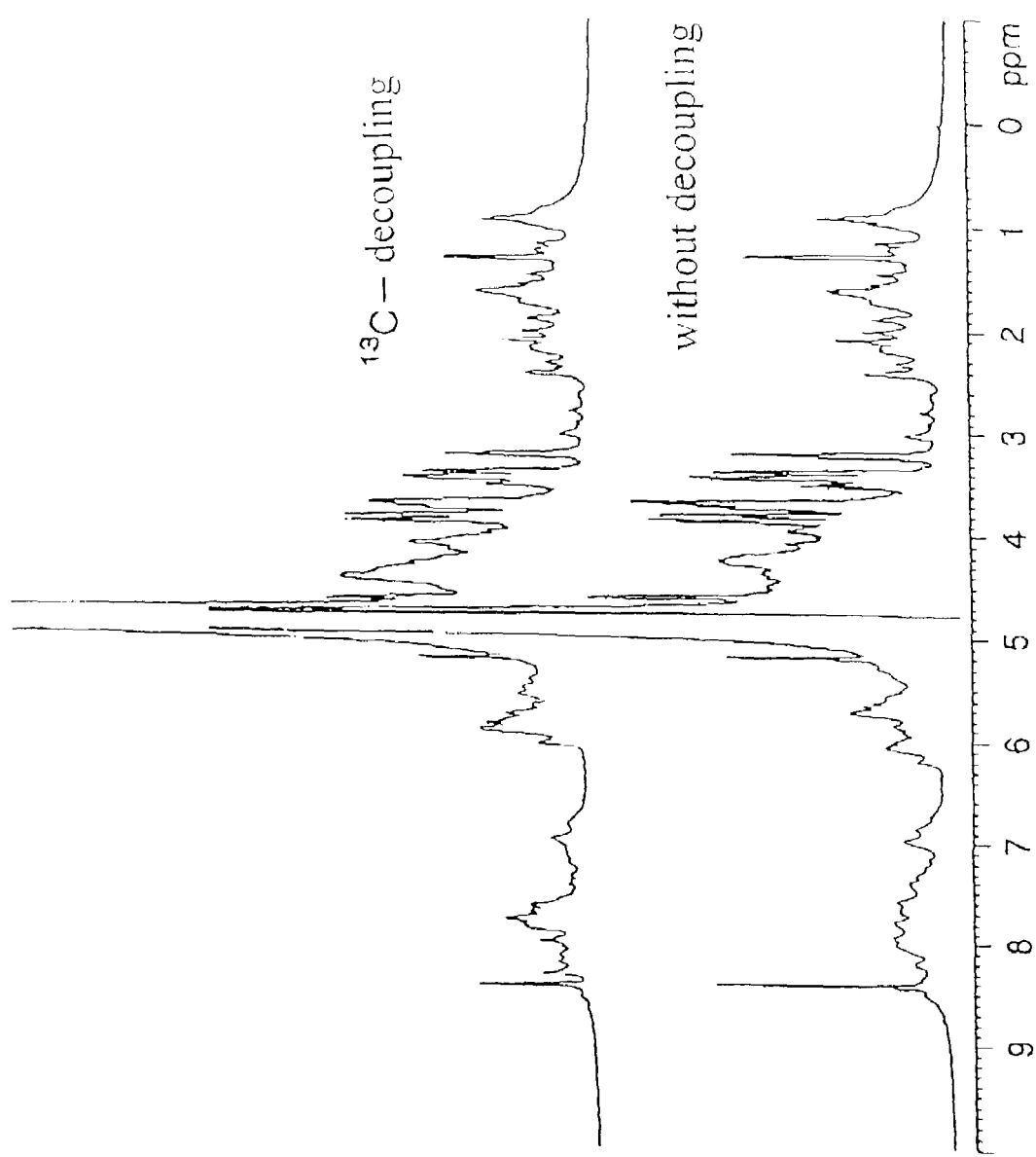
FIG. 12 shows 500 MHz $^1$H-NMR spectra of non-exchangeable protons for sample 4.
Figure 15:
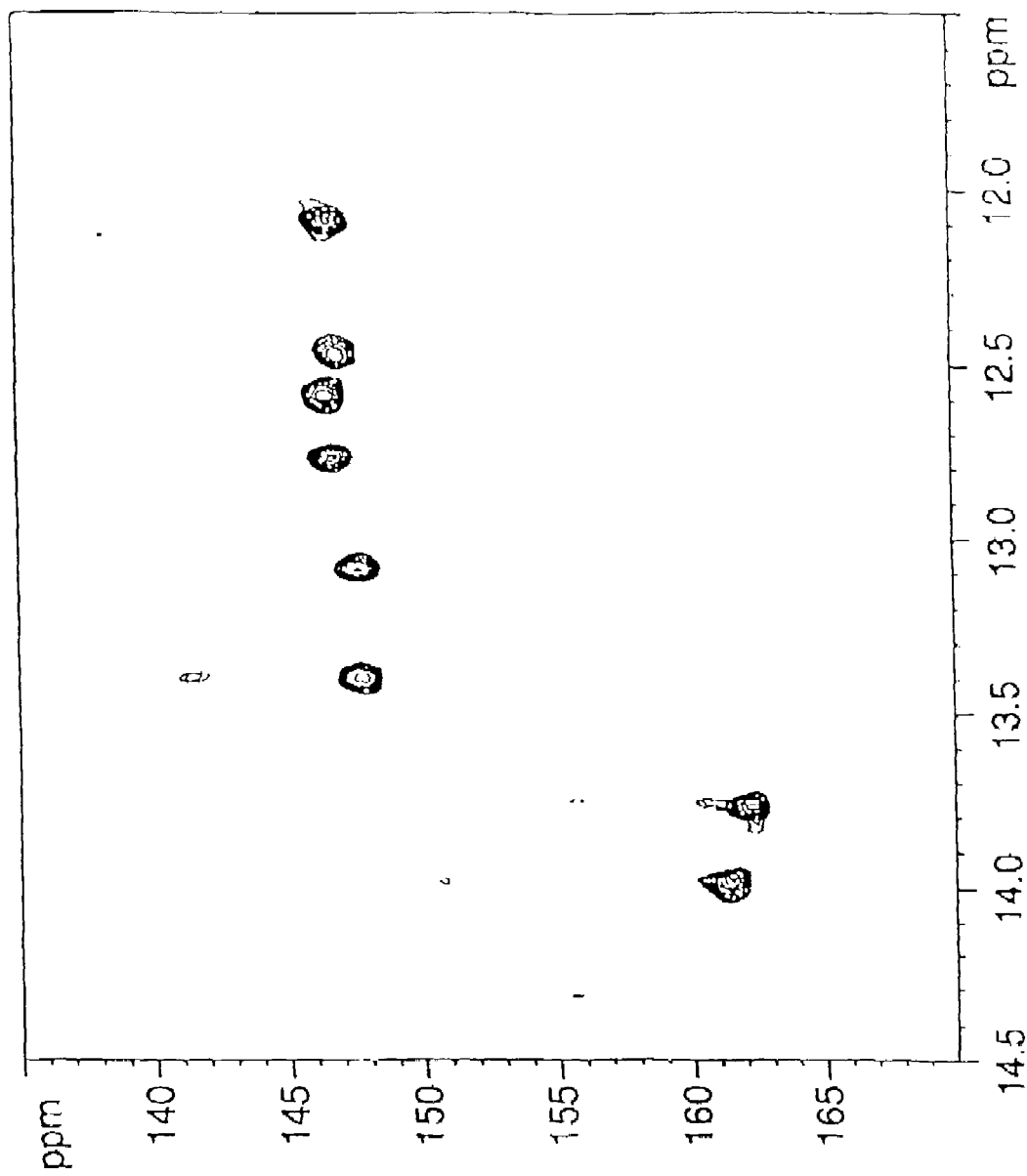
FIG. 15 shows 500 MHz $^{15}$N—$^1$H HMQ spectra of non-exchangeable protons for sample 4.

FIGS. 11 and 15 show the $^{15}$N—$^1$H HMQC spectra of non-exchangeable protons for samples 3 and 4. The vertical axis is the $^{15}$N chemical shift and the horizontal axis is the $^1$H chemical shift. These figures show that the measured RNA was chemically and structurally homogeneous.

EFFECTIVENESS OF THE INVENTION

Since the antisense chain of the present invention has a natural or non-natural nucleotide or peptide nucleic acid as a structural unit and carbon atoms or nitrogen atoms are substituted by stable isotopes, i.e., $^{13}$C or $^{15}$N, the antisense chain can be quantitatively measured, with the lapse of time, by nuclear magnet resonance spectrometry such as $^{15}$N—$^1$H and $^{13}$C—$^1$H heteronuclide multiple quantum coherence spectrometry, or magnetic resonance imaging according to the detection method of the present invention, and the formation of double strand chains can also be detected. Furthermore, the distribution of the antisense chain in the body, or the like, can be analyzed, with the lapse of time, without having to sample a material from the subject animal.

oligonucleotide sequence or antisense peptide nucleic acid sequence having a sequence complementary to a desired target sequence to form a hybrid is administered, or a step of sampling subject culture cells to which an antisense oligonucleotide sequence or antisense peptide nucleic acid sequence having a sequence complementary to a desired target sequence to form a hybrid is administered, and a step of measuring the antisense oligonucleotide sequence or decomposition products thereof, or the antisense peptide nucleic acid sequence or decomposition products thereof derived from said sampled material, by nuclear magnetic resonance spectrometry, said antisense oligonucleotide sequence or antisense peptide nucleic acid sequence being the abovementioned antisense oligonucleotide sequence or antisense peptide nucleic acid sequence comprising a single strand RNA or single strand DNA containing at least one nucleotide or peptide nucleic acid as a structural unit, in which at least one structural C atom is substituted by $^{13}$C, and at least one structural N atom is substituted by $^{15}$N, having 10 to 100 bases complementary to the desired target sequence to be hybridized, said oligonucleotide being i) a phosphodiester oligonucleotide wherein 3'-OH and 5'-OH in ribose or deoxyribose are cross-linked by phosphodiester bonds, ii) a phosphorothioate oligonucleotide wherein one or two non cross-linked oxygen atoms in the phosphodiester bonds in said phosphodiester oligonucleotide are substituted by sulfur atoms, or iii) a methylphosphonate oligonucleotide wherein oxygen atoms in the hydroxyl groups in the phosphodiester bonds in said phosphodiester oligonucleotide are substituted by methyl groups, and said peptide nucleic acid having bases, i.e., purine or pyrimidine, and

What is claimed is:

1. A method of detecting an antisense oligonucleotide sequence containing stable isotopes, or decomposition products thereof, or an antisense peptide nucleic acid sequence containing stable isotopes, or decomposition products thereof, comprising a step of sampling at least one material to be measured, i.e., blood, tissues, organs, body fluids, cells or excretions from a subject animal to which an antisense said bases being linked together by peptide bonds to form a 2-aminoethylglycine backbone, wherein more than 90% of the carbon atoms are substituted by $^{13}$C and more than 90% of the nitrogen atoms are substituted by $^{15}$N in every structural unit, i.e., nucleotide or peptide nucleic acid.

2. A method of detecting an antisense oligonucleotide sequence containing stable isotopes, or decomposition products thereof, or an antisense peptide nucleic acid sequence containing stable isotopes, or decomposition products thereof, comprising a step of sampling at least one material to be measured, i.e., blood, tissues, organs, body fluids, cells or excretions from a subject animal to which an antisense oligonucleotide sequence or antisense peptide nucleic acid sequence having a sequence complementary to a desired target sequence to form a hybrid is administered, or a step of sampling subject culture cells to which an antisense oligonucleotide sequence or antisense peptide nucleic acid sequence having a sequence complementary to a desired target sequence to form a hybrid is administered, and a step of measuring the antisense oligonucleotide sequence or decomposition products thereof, or the antisense peptide nucleic acid sequence or decomposition products thereof derived from said sampled material, by nuclear magnetic resonance spectrometry, said antisense oligonucleotide sequence or antisense peptide nucleic acid sequence being the abovementioned antisense oligonucleotide sequence or antisense peptide nucleic acid sequence comprising a single strand RNA or single strand DNA containing at least one nucleotide or peptide nucleic acid as a structural unit, in which at least one structural C atom is substituted by $^{13}C$, and at least one structural N atom is substituted by $^{15}N$, having 10 to 100 bases complementary to the desired target sequence to be hybridized, said oligonucleotide being i) a phosphodiester oligonucleotide wherein 3'-OH and 5'-OH in ribose or deoxyribose are crosslinked by phosphodiester bonds, ii) a phosphorothioate oligonucleotide wherein one or two non cross-linked oxygen atoms in the phosphodiester bonds in said phosphodiester oligonucleotide are substituted by sulfur atoms, or iii) a methylphosphonate oligonucleotide wherein oxygen atoms in the hydroxyl groups in the phosphodiester bonds in said phosphodiester oligonucleotide are substituted by methyl groups, and said peptide nucleic acid having bases, i.e., purine or pyrimidine, and said bases being linked together by peptide bonds to form a 2-aminoethylglycine backbone, wherein all carbon atoms are substituted by $^{13}C$ and all nitrogen atoms are substituted by $^{15}N$ in every structural unit, i.e., nucleotide or peptide nucleic acid.

* * * * *